United States Patent
Hegazi et al.

(10) Patent No.: US 10,048,205 B2
(45) Date of Patent: Aug. 14, 2018

(54) CHARACTERIZING PETROLEUM PRODUCT CONTAMINATION USING FLUORESCENCE SIGNAL

(71) Applicant: Saudi Arabian Oil Company, Dhahran (SA)

(72) Inventors: Ezzat Hegazi, Ontario (CA); Vincent Cunningham, Ferbane (IE); Christof Brunner, Zurich (CH); Christoph Stamm, Stein am Rhein (CH)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/485,803

(22) Filed: Apr. 12, 2017

(65) Prior Publication Data
US 2017/0299516 A1    Oct. 19, 2017

Related U.S. Application Data

(60) Provisional application No. 62/322,470, filed on Apr. 14, 2016.

(51) Int. Cl.
*G01N 21/64* (2006.01)
*G01N 33/28* (2006.01)

(52) U.S. Cl.
CPC .......... *G01N 21/645* (2013.01); *G01N 33/28* (2013.01); *G01N 2021/6463* (2013.01); *G01N 2201/0621* (2013.01); *G01N 2201/0696* (2013.01)

(58) Field of Classification Search
CPC .................. G01N 21/645; G01N 33/28; G01N 2201/0621; G01N 2201/0696; G01N 2021/6463
See application file for complete search history.

(56) References Cited

U.S. PATENT DOCUMENTS 845,585 A    2/1907    Sharts
3,566,101 A    2/1971    Hagner
(Continued)

FOREIGN PATENT DOCUMENTS

CA    2711801 A1    7/2009
EP    0506063      9/1992
(Continued)

OTHER PUBLICATIONS

International Search Report and Written Opinion issued in International Application No. PCT/US2017/027140 dated Sep. 15, 2017; 21 pages.
(Continued)

*Primary Examiner* — Mark R Gaworecki
(74) *Attorney, Agent, or Firm* — Fish & Richardson P.C.

(57) ABSTRACT

Methods and systems for determining contamination in a petroleum-based sample, including irradiating the petroleum-based sample with a light beam from a light source such that a fluorescence signal is generated, guiding, by a mirror, the fluorescence signal to a gear-less rotating diffraction grating, the gear-less rotating diffraction grating spatially separating a fluorescence wavelength from the florescence signal, detecting, by an optical detector, fluorescence wavelength, transforming the fluorescence wavelength into a spectral contour diagram, the spectral contour diagram comprising a fluorescence wavelength variation over time, and determining, the contamination in the petroleum-based sample using the spectral contour diagram.

22 Claims, 11 Drawing Sheets
(4 of 11 Drawing Sheet(s) Filed in Color)

(56) References Cited

U.S. PATENT DOCUMENTS

| | | |
|---|---|---|
| 3,594,083 A | 7/1971 | Barringer |
| 3,841,769 A | 10/1974 | Bowerman |
| 3,981,566 A | 9/1976 | Frank et al. |
| 4,023,891 A | 6/1977 | Chadwick |
| 4,031,398 A | 6/1977 | Callis et al. |
| 4,060,314 A | 11/1977 | Heinz |
| 4,060,315 A | 11/1977 | Heinz |
| 4,398,798 A | 8/1983 | Krawczak et al. |
| 4,497,465 A | 2/1985 | Yeakley et al. |
| 4,651,010 A | 3/1987 | Javan |
| 4,655,543 A | 4/1987 | Montagu |
| 4,664,487 A | 5/1987 | Tam |
| 4,991,815 A | 2/1991 | Softness |
| 5,283,682 A | 2/1994 | Ostaszewski |
| 5,422,719 A | 6/1995 | Goldstein |
| 5,818,582 A | 10/1998 | Fernandez et al. |
| 6,519,034 B1 | 2/2003 | Engler et al. |
| 6,525,325 B1 | 2/2003 | Andrews et al. |
| 6,633,043 B2 | 10/2003 | Hegazi et al. |
| 7,009,752 B1 | 3/2006 | Lorell et al. |
| 8,240,941 B2 | 8/2012 | Kibel |
| 2002/0158211 A1 | 10/2002 | Gillispie |
| 2003/0133105 A1 | 7/2003 | Gorelik et al. |
| 2004/0007675 A1 | 1/2004 | Gillispie et al. |
| 2004/0124366 A1 | 7/2004 | Zeng et al. |
| 2005/0135874 A1 | 6/2005 | Baylis et al. |
| 2006/0274811 A1 | 12/2006 | Tanaka et al. |
| 2008/0173804 A1 | 7/2008 | Ndo et al. |
| 2009/0006004 A1 | 1/2009 | Sens et al. |
| 2011/0303834 A1 | 12/2011 | Hegazi et al. |
| 2012/0034027 A1 | 2/2012 | Valois |
| 2012/0057254 A1 | 3/2012 | Arnone et al. |
| 2014/0198313 A1 | 7/2014 | Tracey et al. |
| 2015/0009495 A1 | 1/2015 | Li et al. |
| 2015/0039265 A1 | 2/2015 | Acharid et al. |
| 2015/0112611 A1 | 4/2015 | Koseoglu |
| 2015/0168368 A1 | 6/2015 | Hegazi et al. |
| 2015/0362694 A1 | 12/2015 | Nguyen et al. |

FOREIGN PATENT DOCUMENTS

| | | |
|---|---|---|
| EP | 0540966 | 5/1993 |
| EP | 1371957 A1 | 12/2003 |
| FR | 2817346 A1 | 5/2002 |
| FR | 2883076 | 9/2006 |
| JP | S60-256108 | 12/1985 |
| JP | H04290933 A | 10/1992 |
| JP | 2010008706 A | 1/2010 |
| JP | 2011106842 A | 6/2011 |

OTHER PUBLICATIONS

Hegazi et al., "Estimation of crude oil grade using time-resolved fluorescence spectra," Talanta, vol. 56, No. 6, Apr. 2002; pp. 989-995.

Hegazi et al., "New approach for spectral characterization of crude oil using time-resolved fluorescence spectra," Applied Spectroscopy, vol. 55, No. 2, Feb. 2001; pp. 202-207.

Pantoja et al., "Prediction of Crude Oil Properties and Chemical Composition by Means of Steady-State and Time-Resolved Fluorescence," Energy Fuels, vol. 25, No. 8, Jul. 2011; pp. 3598-3604.

Ralston et al., "Quantum yields of crude oils," Applied Spectroscopy, vol. 50, No. 12, Dec. 1996; pp. 1563-1568.

Ryder, "Time-resolved fluorescence spectroscopic study of crude petroleum oils: Influence of chemical composition," Applied Spectroscopy, vol. 58, No. 5, May 2004; pp. 613-623.

Ryder et al., "Characterization of crude oils using fluorescence lifetime data," Spectrochimica Acta A, vol. 58, No. 5, Mar. 2002; pp. 1025-1037.

Wang et al., "Fluorescence Lifetime Studies of Crude Oils," Applied Spectroscopy, vol. 48, No. 8, Aug. 1994; pp. 977-984.

International Search Report and Written Opinion issued in International Application No. PCT/US2017/027132 dated Jul. 5, 2017; 12 pages.

Invitation to Pay Additional Fees and Partial International Search Report issued in International Application No. PCT/US2017/027140 dated Jul. 24, 2017; 12 pages.

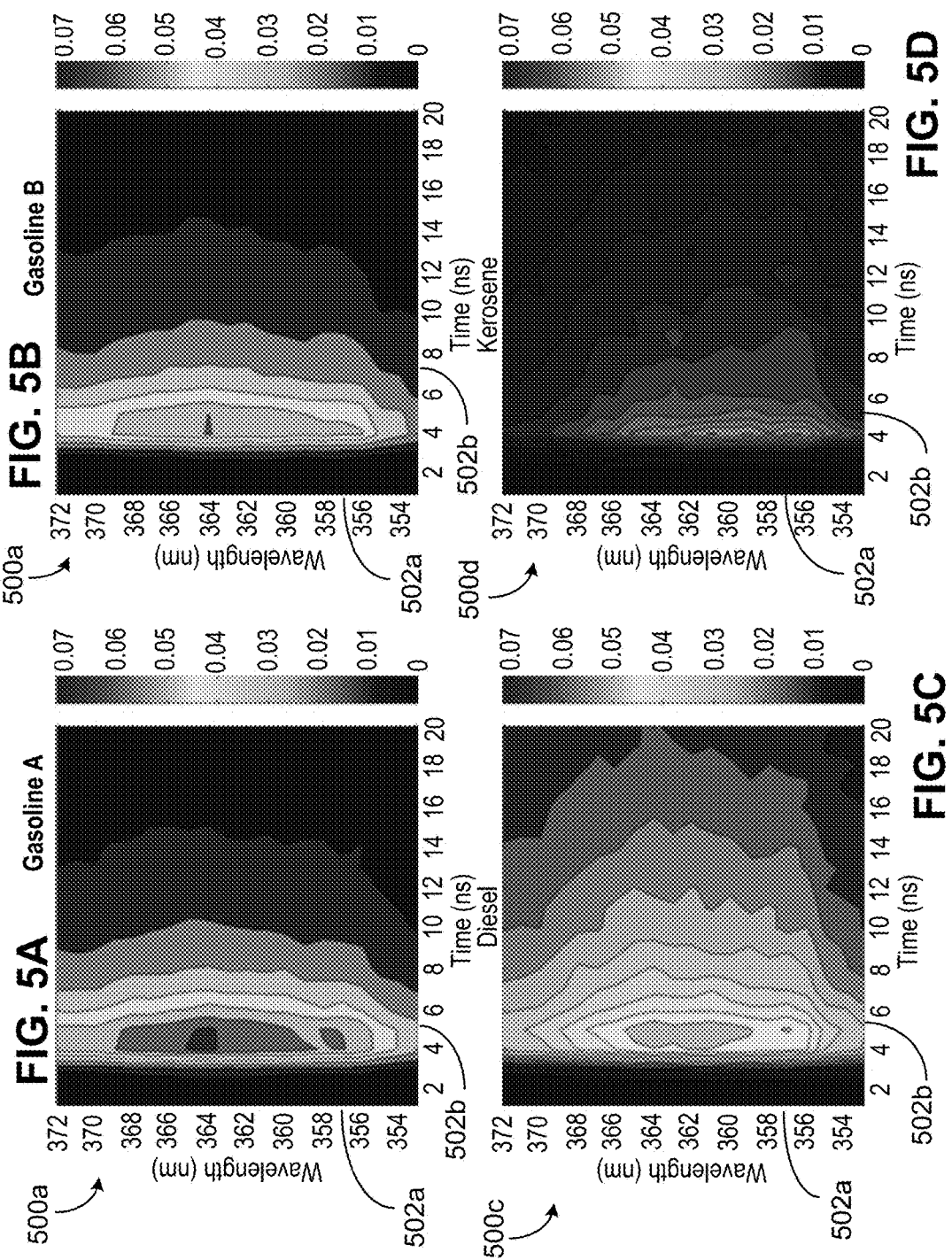

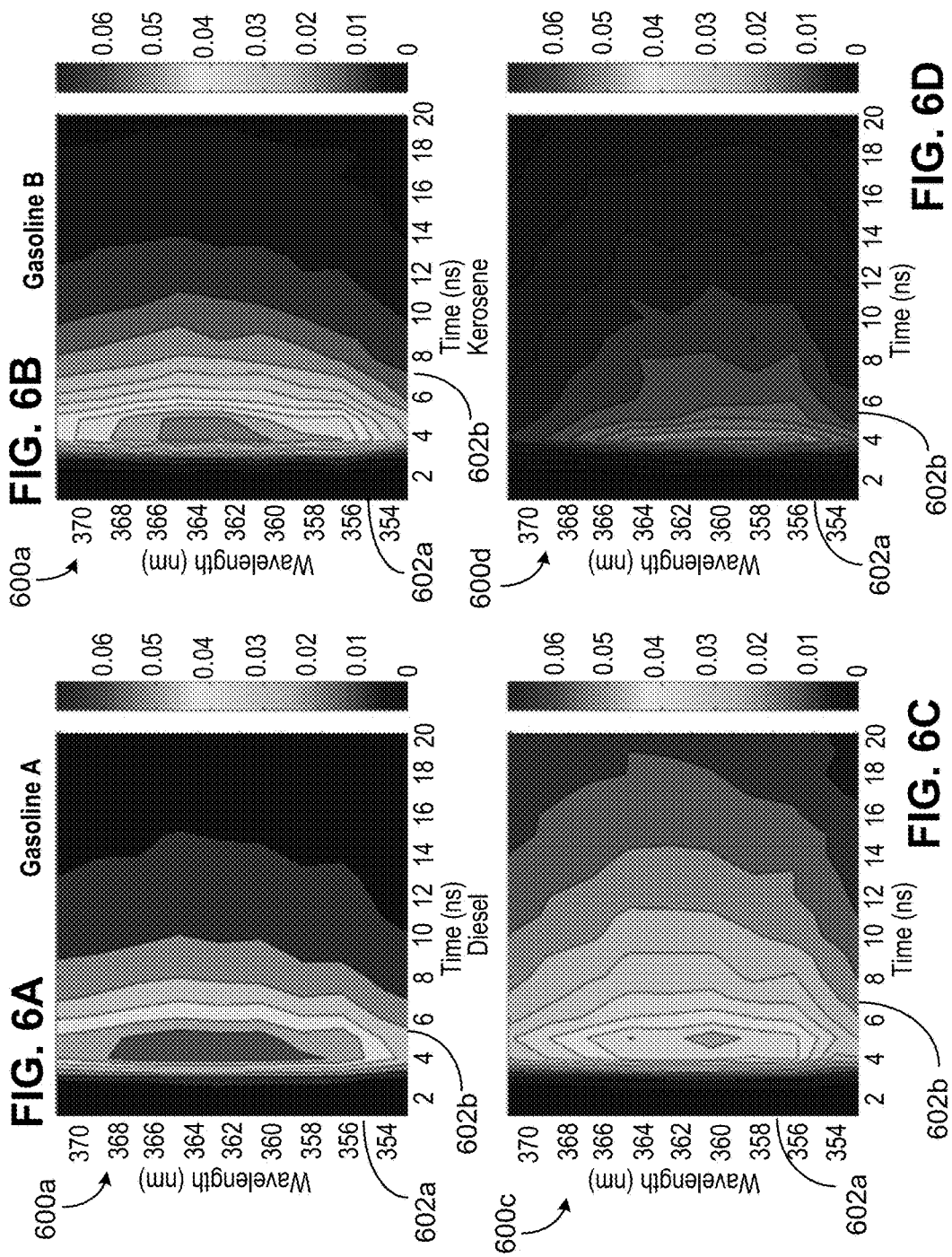

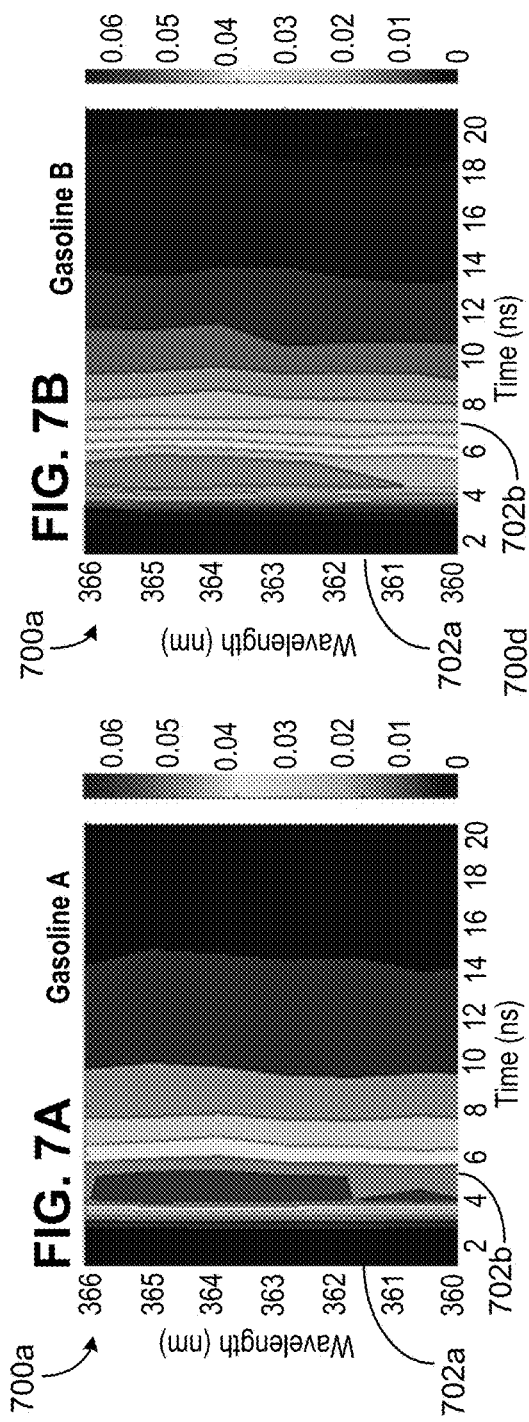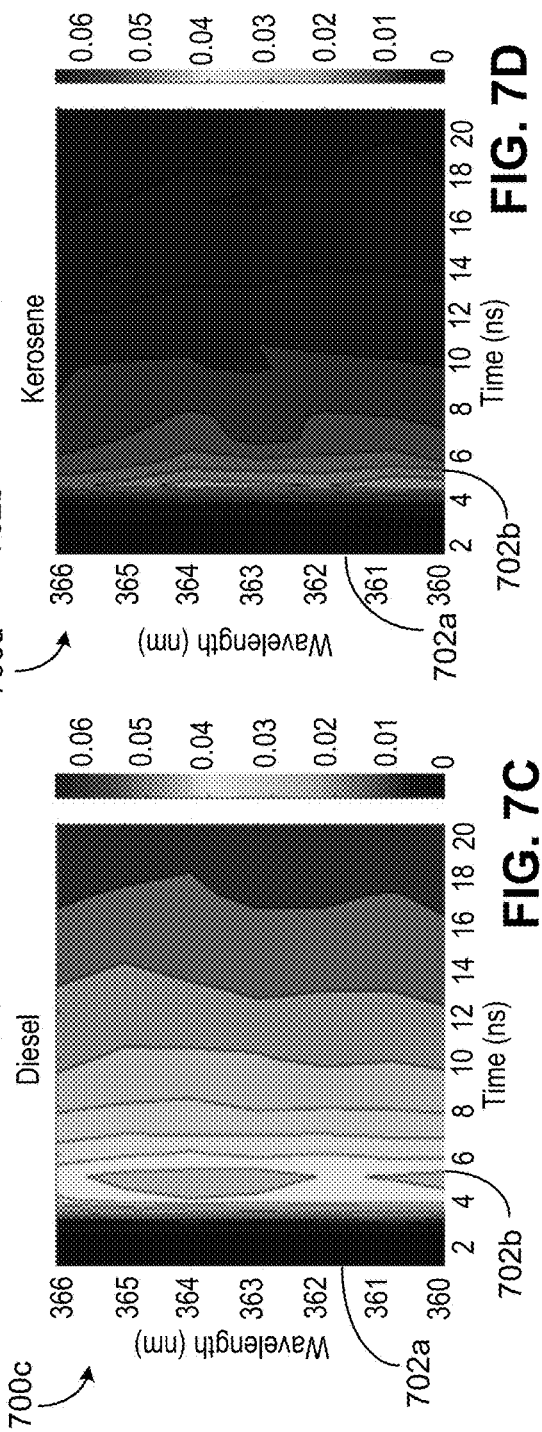

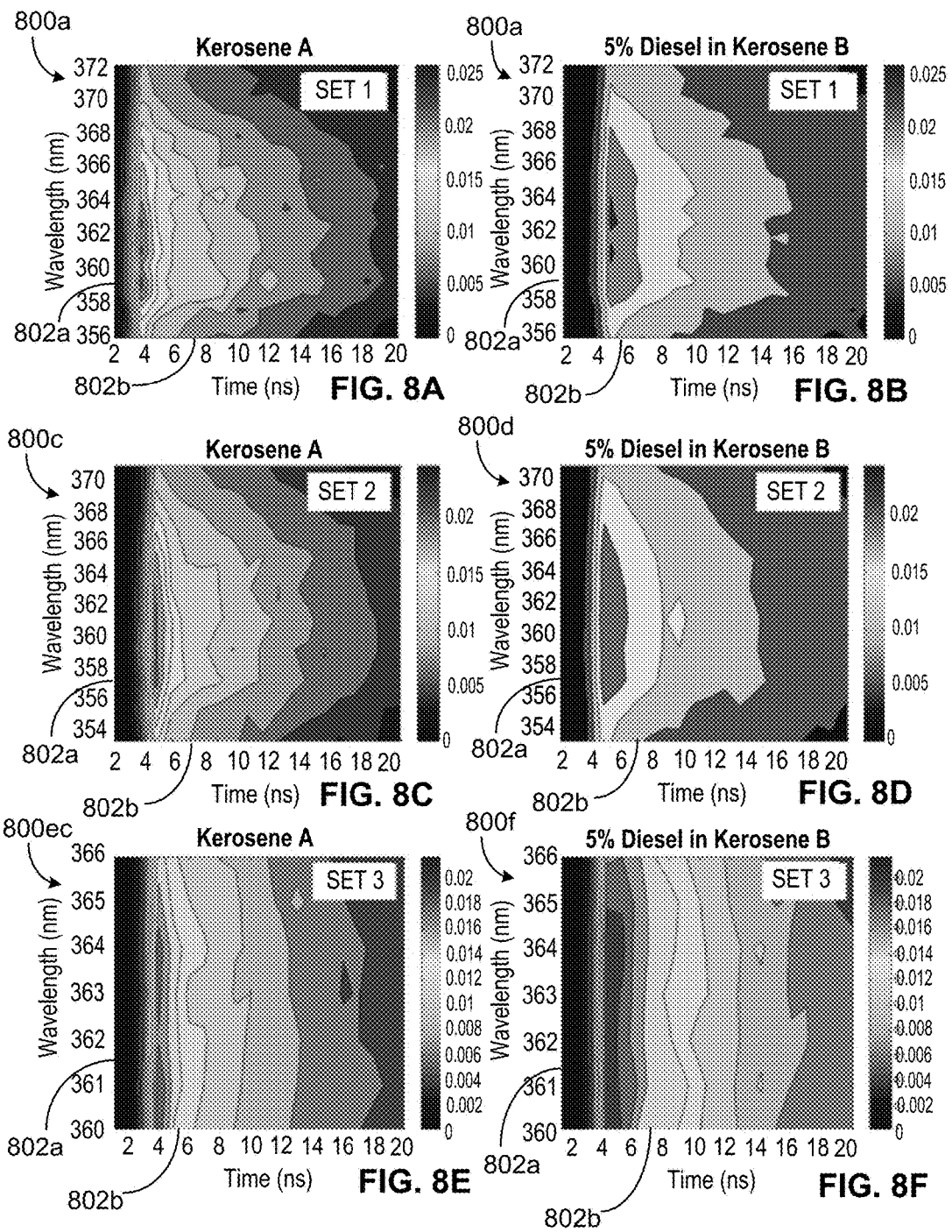

CHARACTERIZING PETROLEUM PRODUCT CONTAMINATION USING FLUORESCENCE SIGNAL

This specification relates to spectroscopy and applications to petroleum products.

BACKGROUND

An oil refinery or petroleum refinery is an industrial process plant where crude oil is processed and refined into multiple different products. Based on the processing methods, oil products can be separated in different classes, such as crude fractions of petroleum products, light refined oil, and heavy residual oil. Crude fractions of petroleum products include natural gasoline, diesel, kerosene, asphalt, vacuum oils, naphtha, coke, and other petroleum products. Refined petroleum products include regular and reformulated gasoline, jet and fuel kerosene, lube oils, number 2 fuel oil, number 6 fuel oil, and other petroleum products. Each type of petroleum product is characterized by a particular type of hydrocarbon molecules. The hydrocarbon molecules of petroleum products can have varying lengths and complexity. The differences in the structure of the hydrocarbon molecules account for their varying physical and chemical properties, making each type of petroleum product useful for particular applications.

Petroleum products are susceptible to contamination. Analytical testing for contaminants in a petroleum fluid is an important step in many industrial processes. Contaminants can be in the form of small amounts of other types of petroleum products, which have remained, for example, in multi-purpose pipelines or refined oil storage tanks. Contaminants can be in the form of small amounts of the same petroleum product but having different sulfur contents, which commonly happens in diesel fuel distribution, operations, and storage. The contaminants can also be in the form of weathered petroleum products mixed with fresh petroleum products or in the form of some chemicals that cannot be readily identified. Identification of contamination of petroleum products can be used to discover contaminant sources, to correct contamination or to prevent future contamination.

SUMMARY

The present specification describes methods and systems for performing oil contamination analysis (OCA) of a petroleum product sample. In some implementations, OCA tests include recording and processing laser-induced fluorescence signal from a petroleum product sample.

In an implementation, a method includes irradiating the petroleum-based sample with a light beam from a light source such that a fluorescence signal can be generated, guiding, by a mirror, the fluorescence signal to a gear-less rotating diffraction grating, the gear-less rotating diffraction grating spatially separating a fluorescence wavelength from the florescence signal, detecting, by an optical detector, fluorescence wavelength, transforming the fluorescence wavelength into a spectral contour diagram, the spectral contour diagram including a fluorescence wavelength variation over time, and determining, the contamination in the petroleum-based sample using the spectral contour diagram.

The foregoing and other implementations can each, optionally, include one or more of the following features, alone or in combination. In an aspect, the sample can be a liquid that can include fluorescent or phosphorescent molecules. The sample can include refined petroleum products or crude petroleum products. The sample can be irradiated with the light beam as the sample flows through the pipeline. The method can further include forming an optical window that can be transparent to the fluorescence signal and the energy light beam in the pipeline. The optical detector can be configured to detect a spectral range from about 350 nanometers to about 700 nanometers in real time. Detecting the fluorescence wavelengths can be performed by a photon counting multi-scaler optoelectronic detector.

In a further aspect, the method can further include determining an optical intensity of the fluorescence signal by correlating a frequency of photon incidences detected by the photon counting multi-scaler optoelectronic detector within pre-defined subsequent time intervals over several periods. The method can further include mounting the gear-less rotating diffraction grating on a rotating axis of an encoded motor. The method can further include selecting, by an integrated decoder, a wavelength of the gear-less rotating diffraction grating. Selecting the wavelength can include rotating the gear-less rotating diffraction grating from a first position to a second position. Selecting the wavelength can include generating a spectral range from about 350 nanometers to about 700 nanometers. Generating the spectral range can be completed in about 2 seconds. The light source can include a light-emitting diode.

In a further aspect, the light beam can have an intensity in a pico-Joule range and can be smaller than 1 nano-Joule. The light beam can be a pulsed light beam. The method can further include generating calibration curves based on samples including pre-known percentages of contamination. Determining the oil contamination based on the spectral contour diagram can include correlating the spectral contour diagram to the calibration curves. Correlating the spectral contour diagram to the calibration curves can be performed for a particular set of optical parameters and a particular set of temporal parameters.

In some implementations, the present disclosure also provides another method for determining contamination in a petroleum-based sample. The method includes generating a fluorescence signal by irradiating a sample with a light beam, guiding the fluorescence signal to a gear-less rotating diffraction grating, detecting, by an optical detector, fluorescence wavelengths spatially separated by the gear-less rotating diffraction grating, processing the fluorescence wavelengths to generate a spectral contour diagram, and determining the oil contamination based on the spectral contour diagram.

In an aspect, the sample can be a liquid that can include fluorescent or phosphorescent molecules. The sample can include refined petroleum products or crude petroleum products. The sample can be irradiated with the light beam as the sample flows through the pipeline. The method can further include forming an optical window that can be transparent to the fluorescence signal and the energy light beam in the pipeline. The optical detector can be configured to detect a spectral range from about 350 nanometers to about 700 nanometers in real time.

In a further aspect, detecting the fluorescence wavelengths can be performed by a photon counting multi-scaler optoelectronic detector. The method can further include determining an optical intensity of the fluorescence signal by correlating a frequency of photon incidences detected by the photon counting multi-scaler optoelectronic detector within pre-defined subsequent time intervals over several periods. The method can further include mounting the gear-less rotating diffraction grating on a rotating axis of an encoded motor. The method can further include rotating the gear-less rotating diffraction grating to generate a spectral range from about 350 nanometers to about 700 nanometers in about 2 seconds.

In a further aspect, the light source can include a light-emitting diode. The light beam has an intensity in a pico-Joule range and can be smaller than 1 nano-Joule. The light beam can be a pulsed light beam. The method can further include generating calibration curves based on samples, including pre-known percentages of contamination. Determining the oil contamination based on the spectral contour diagram can include correlating the spectral contour diagram to the calibration curves.

In some implementations, the present disclosure also provides a system to diagnose an oil contamination, the system including: a gear-less rotating diffraction grating configured to receive a fluorescence signal generated by irradiating a petroleum-based sample with a light beam, the gear-less rotating diffraction grating configured to spatially separate a fluorescence wavelength from the fluorescence signal, an optical detector configured to detect a fluorescence wavelength separated from the fluorescence signal by the gear-less rotating diffraction grating, and an optical signal processor. The optical signal processor can be configured to perform operations including: transforming the fluorescence wavelength into a spectral contour diagram, the spectral contour diagram including a fluorescence wavelength variation over time and determining the contamination in the petroleum-based sample using the spectral contour diagram.

In an aspect, the sample can be a liquid that can include fluorescent or phosphorescent molecules. The sample can include refined petroleum products or crude petroleum products. The sample can be irradiated with the light beam as the sample flows through the pipeline. The optical detector can be configured to detect a spectral range from about 350 nanometers to about 700 nanometers in real time. The light source can include a light-emitting diode. The light beam has an intensity in a pico-Joule range and can be smaller than 1 nano-Joule. The light beam can be a pulsed light beam.

In some implementations, the present disclosure also provides another method to diagnose an oil contamination, the method including: generating a fluorescence signal by irradiating a sample with a light beam, guiding the fluorescence signal to a narrow band filter, filtering, by the narrow band filter, the fluorescence signal to obtain a filtered fluorescence signal, detecting, by an optical detector, the filtered fluorescence signal, processing, by one or more processors, the filtered fluorescence signal to generate a spectral contour diagram, and determining the oil contamination based on the spectral contour diagram.

In an aspect, the sample can be a liquid that can include fluorescent or phosphorescent molecules. The sample can include refined petroleum products or crude petroleum products. The sample can be irradiated with the light beam as the sample flows through the pipeline. The method can further include forming an optical window that can be transparent to the fluorescence signal and the energy light beam in the pipeline. Filtering, by the narrow band filter, the fluorescence signal can include concentrating the fluorescence signal to a narrow region of a fluorescence spectrum. The light source can include a light-emitting diode. The light beam has an intensity in a pico-Joule range and can be smaller than 1 nano-Joule. The light beam can be a pulsed light beam. The method can further include generating calibration curves based on samples including pre-known percentages of contamination. Determining the oil contami-nation based on the spectral contour diagram can include correlating the spectral contour diagram to the calibration curves.

The details of one or more implementations of the subject matter of this specification are set forth in the accompanying drawings and associated description. Other features, aspects, and advantages of the subject matter will become apparent from the description, the drawings, and the claims.

DESCRIPTION OF DRAWINGS

The patent or application file contains at least one drawing executed in color. Copies of this patent or patent application publication with color drawing(s) will be provided by the Patent and Trademark Office upon request and payment of the necessary fee.

FIGS. 5A-5D illustrate example charts of contours of equal fluorescence intensities of the time-resolved fluorescence spectra for different petroleum products using a first number of wavelengths.

FIGS. 6A-6D illustrate example charts of contours of equal fluorescence intensities of the time-resolved fluorescence spectra for different petroleum products using different numbers of wavelengths FIGS. 7A-7D illustrate example charts of contours of equal fluorescence intensities of the time-resolved fluorescence spectra for different petroleum products using different numbers of wavelengths.

FIGS. 8A-8F illustrate example charts of contours of equal fluorescence intensities of the time-resolved fluorescence spectra for different contaminated petroleum products using different numbers of wavelengths.

DETAILED DESCRIPTION

Figure 1:
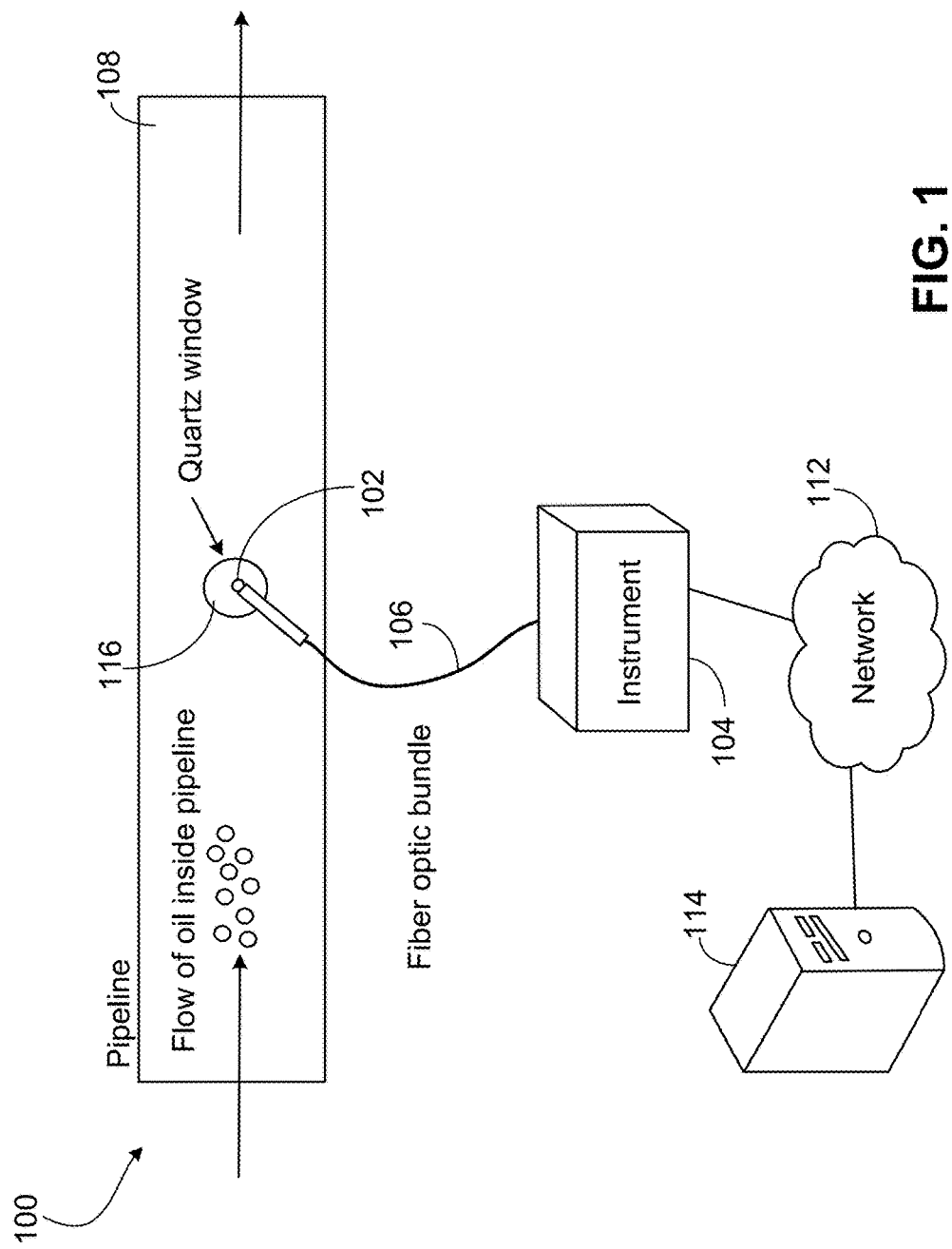
FIG. 1 is a diagram illustrating an example system for characterizing petroleum product contamination using fluorescence signals.

Currently, the identification of petroleum product contamination provides the best possible detection for contamination sources and early warning of inefficient combustion of the petroleum products. However, the majority of industries use offsite and offline oil contamination analysis (OCA) to quantify oil contaminants. It would be beneficial to have an accurate, efficient, and rapid ability to perform onsite OCA, for example in the proximity of a pipeline transporting petroleum products.

OCA is a process used to derive one or more characteristics (for example, contamination type and contamination degree) of a contaminated petroleum product, such as a petroleum product sample including a petroleum product base and a contaminant. In some implementation, OCA can be applied to evaluate the quality of petroleum processing techniques. In the evaluation of the quality of petroleum processing techniques, the petroleum product base and the contaminant can be different grades of oils belonging to the same broad class, such as light crude oil and medium crude oil. The identification of contaminants in petroleum product sample during mid-stream petroleum processing can provide relevant data for reprocessing the analyzed petroleum product to eliminate the contaminant. In some implementations, OCA can be applied to evaluate the preservation of quality of refined petroleum products during transportation from the refinery to a different location for sale. In transportation contamination, the contaminant can be associated to a characteristic of the container or pipeline used for transportation of the petroleum product. For example, shipping containers of barges and boats can have malfunctioning sealing mechanisms that allow contamination of the petroleum oils with salts. Some pipelines and storage tanks can be designed for multi-purpose transportation. In multi-purpose pipelines or refined oil storage tanks, contaminants can be in the form of small amounts of the same refined petroleum product having different sulfur contents, which commonly happens in diesel fuel distribution operations and storage. In multi-purpose pipelines or refined oil storage tanks, contaminants can also be in the form of weathered refined petroleum products mixed with fresh refined petroleum products or in the form of some chemicals (such as water) that infiltrated within the pipeline or the container. In addition, in multi-purpose pipelines or refined oil storage tanks, contamination can also be due to accidental mixing between two different products such as diesel and kerosene.

Changes over time in the OCA data in petroleum product samples from one or more parts of the pipeline can provide useful information to determine the occurrence and location of a contamination source and also to divert the contaminated product away from the non-contaminated storage location. The normal practice for comparing and validating available oil contamination analysis data is to leverage technical skill or expertise to numerically interpret oil contamination analysis data, but does not leverage correlations or relationships that can be efficiently derived from available oil contamination analysis data and rapid measurement of contamination oil characteristics. It is important to have an efficient, rapid, and simple ability to derive up-to-date data based on prior OCA oil contamination analysis data in order to be able to perform special analysis studies and to determine, for example and among other things, the earlier-mentioned contamination trends and reduction or increase of petroleum product contamination.

At a high level, this specification generally describes methods and systems, including methods, products, and systems, for predicting contamination of a refined petroleum product by using a spectrometer. In particular, OCA includes irradiating a sample of the refined petroleum product with a light beam from a light source. The sample of the refined petroleum product generates a fluorescence signal, which can be guided, by a mirror or fiber optic, to the spectrometer to detect and process the fluorescence signal and to determine the oil contamination.

The core of the spectrometer can be an optical dispersive element, which can resolve the fluorescence signal generated by the petroleum product. The optical dispersive element is critical for the resolution and the speed of the system. The optical dispersive element is generally composed of a diffraction grating or prism that spatially separates the desired wavelengths and projects the wavelengths to an optical detector. As a result of the superior dispersion properties, diffraction gratings are the common choice for high resolution spectrometers. The grating relies on the difference in direction of each wavelength due to interference, whereas the prism resolves the fluorescence signal from changes in refractive index. The mirrors and other optical elements in the spectrometer project the spatially separated wavelengths (from rotation selection) onto the optical detector to perform the optoelectronic conversion required to quantify the spectral intensity of each wavelength and fluorescence lifetime.

The spectral intensity of each wavelength, can be used to predict contamination of a refined petroleum product. The prediction accuracy of the contamination can be further enhanced by complementing the spectral measurement with time-decay information at each dispersed wavelength in the spectral range. Particularly, the predictions are based on a comparison of contour plots of the fluorescence wavelength emission (y-axis), time decay (x-axis) and optical intensity of the petroleum product sample to contour plots of known petroleum product types. The methods and the systems described in this specification can be implemented to diagnose oil contamination by directly sampling the petroleum product flowing through a pipeline, on a regular basis, such as a daily basis, at low costs, non-intrusively, on-line, and in real-time (by providing the results within seconds from data acquisition). OCA can include a high-resolution identification of contamination type and a quantitative estimate of the contamination, which can be leveraged to identify and eliminate contamination sources. OCA can be performed directly on adapted pipelines, without requiring the extraction of a sample from the pipeline.

The optical detection scheme in a spectrometer is critical for the resolution of the measurement and it also determines the lower limit on the fluorescence intensity and the speed by which a specific spectrum range is measured. The choice of detector depends on both the spectral range of interest, the speed of measurement, and the intensity of the dispersed light. Optical spectrometers are found in two different configurations, one with fixed diffraction grating and a second with rotating diffraction grating. By using a fixed diffraction grating the spatially separated wavelengths can be projected onto a detector array, such as a charge coupled device (CCD) or an intensified charge coupled device (ICCD) to measure the full spectral range instantly. By using a rotating diffraction grating, each dispersed wavelength is projected onto a single detector element (for example, a PMT or a photon counting multi-scaler optoelectronic detector) and the full spectral range is produced when the rotation of the diffraction grating is completed. The faster the rotation the faster the full spectral range can be measured. The choice of spectrometer is application dependent as each configuration has its inherent advantages and disadvantages. The mechanical robustness of the array spectrometer is superior as it only requires a single moving part (for example, a shutter) allowing for a rapid snapshot of the fluorescing light. However, the electrical stability and high detection sensitivity of the rotating diffraction grating+PMT scheme prevails over that of the fixed diffraction grating+ICCD scheme. The advantages of using a rotating diffraction grating scheme are associated to the complex architecture of ICCD detector, that requires cooling, and that displays differences in pixel to pixel sensitivity, which is known to change over the lifetime of the detector. Another limitation presented by the array detector elements is the resolution limitation that is determined by the size of the pixel. In the single detector scheme the resolution limitation is controlled by a slit. As a result of advances in detector technology, particularly photon counting techniques, the rotating diffraction grating configuration can provide a superior signal to noise ratio and more controllable resolution. In addition, a fast rotating diffraction grating can provide the necessary fast spectrum range measurement. The rotating diffraction grating can be replaced by a narrow band filter. The advantage of the narrow band filter are (1) the size of the integrated instrument can be less than half and (2) the instrument does not include any mechanical motors.

In some implementations, OCA can be used to automatically predict a quantitative value of the contaminant volume, expressed as percentage relative to the total volume of the analyzed petroleum product. The use of OCA is an easy, efficient, and time saving process of comparing and validating available OCA oil contamination analysis data. OCA can be associated to multiple performed actions that include determination of leaks within a pipeline or between two refined petroleum product reservoirs, performing remedial or proactive actions based on OCA oil contamination analysis data correlations, predictions, or other performed actions. OCA can enhance the efficiency of the performed actions based on OCA oil contamination analysis data that can be derived or predicted from rapid and simple measurement of contamination oil fluorescence. Multiple oil samples flowing through the same position of a pipeline at different times (for example, during a time interval in which the pipeline was not modified) can be used to generate a graphical correlation of respective OCAs. The graphical correlation of multiple OCAs can provide data useful for monitoring contamination trends. For example, the described approach for correlating or relating, displaying, and predicting data pertaining to OCAs can be used by one or more elements of an organization to develop different actions particular to their assigned function for the organization.

FIG. 1 is a diagram illustrating an example of a system 100 provided by the present specification. The system 100 of FIG. 1 can be implemented to perform OCA and to derive the contour plot of the fluorescence wavelength emission associated to the analyzed petroleum product sample 102. The example components of the system 100 can include an optical instrument 104, a fiber optic bundle 106, a container 108, a network 112, and a computing system 114.

The optical instrument 104 can include a laser source, as described in detail with reference to FIGS. 2A and 2B. In some implementations, the optical instrument 104 can generate a light beam as pulsed electromagnetic waves. The light beam can be guided towards the container 108 by the fiber optic bundle 106. The container 108 can be a pipeline through which a petroleum product is flowing or a quartz cuvette, in which a petroleum product sample is stored. The container 108 can include an optical window 116. For example, the container 108 can include walls or a portion of a wall that are transparent to the central emission wavelength (for example, 350 nanometers). The container can have multiple geometries that provide at least one planar side (for example, a planar optical window 116) that enables optimization of the irradiation of the petroleum product. For example, the container 108 can be square-shaped or rectangular shaped. The optical window 116 can be a quartz window or any other type of optical window that is transparent to a central wavelength of the light beam generated by the optical instrument 104.

The petroleum product sample 102, irradiated by the light beam, generates a laser-induced fluorescence signal. The fluorescence signal of the petroleum product sample 102 can be redirected to the fiber optic bundle 106. The optical fiber 106 can transfer the fluorescence signal to the optical instrument 104 to capture the fluorescence intensity as function of time. An output signal of the optical instrument 104 can be transmitted over a network 112 to a computing system 114. The computing system 114 can acquire, record and process the fluorescence signal.

Data post processing can include smoothing, reduction of redundant information, and correlation algorithms (for example, process 400 described with reference to FIG. 4). In some implementations, the computing system 114 can be a mobile handheld device. In some examples, the computing system 114 and the optical instrument 104 can be directly connected to and powered by an external power source (for example, a wall outlet).

In some implementations, the computing system 114 can include a trigger source that is a computer program operable to control one or more of a start time and an end time for data acquisition. In some examples, the trigger source can be determined by an algorithm stored within a computer-readable memory of the computing system 114. In some implementations, the system 100 can include a trigger source that is housed external to, and separately from, the computing system 114 or affixed to the optical instrument 104. For example, the trigger source can be a foot pedal, a switch, a button, or a lever that allows a user of the system 100 to activate the trigger source by depressing the pedal, flipping the switch, depressing the button, or moving the lever, respectively. In some examples, the trigger source is operable to cause the optical instrument 104 to deliver a laser beam with particular characteristics to the petroleum product sample 102 when the trigger source is activated by the user of the system 100.

The results can be displayed to a user of the system 100 as a contour plot of the fluorescence wavelength emission (y-axis), time decay (x-axis) and optical intensity. The optical intensity can be obtained by correlating the frequency of photon incidences that occur within clearly defined subsequent time intervals over several periods. Contour plots enable comparative analysis of the different fluorescence spectra.

Figure 2A:
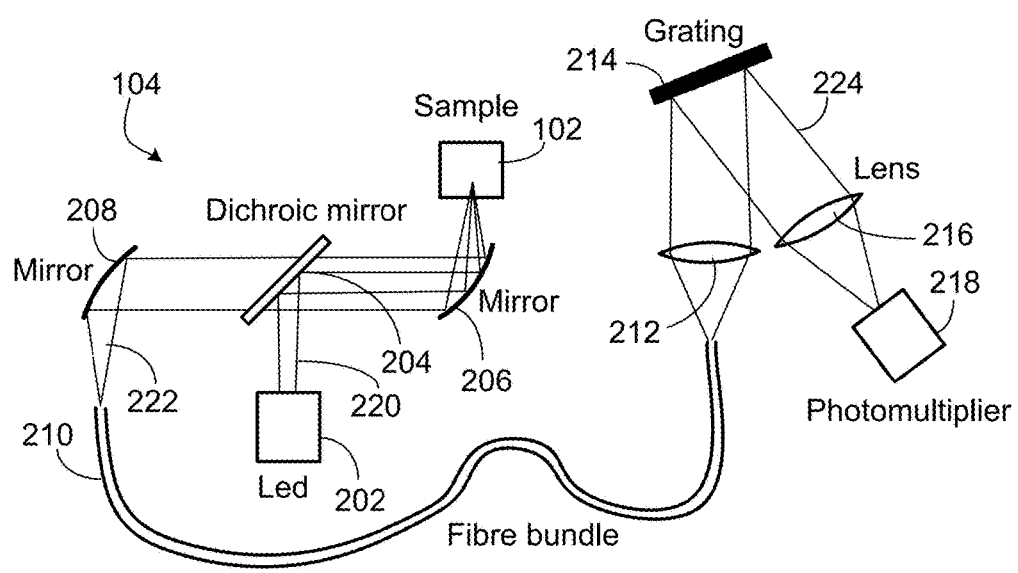
FIGS. 2A and 2B are diagram illustrating examples of a system for characterizing petroleum product contamination using fluorescence signals.
Figure 2B:
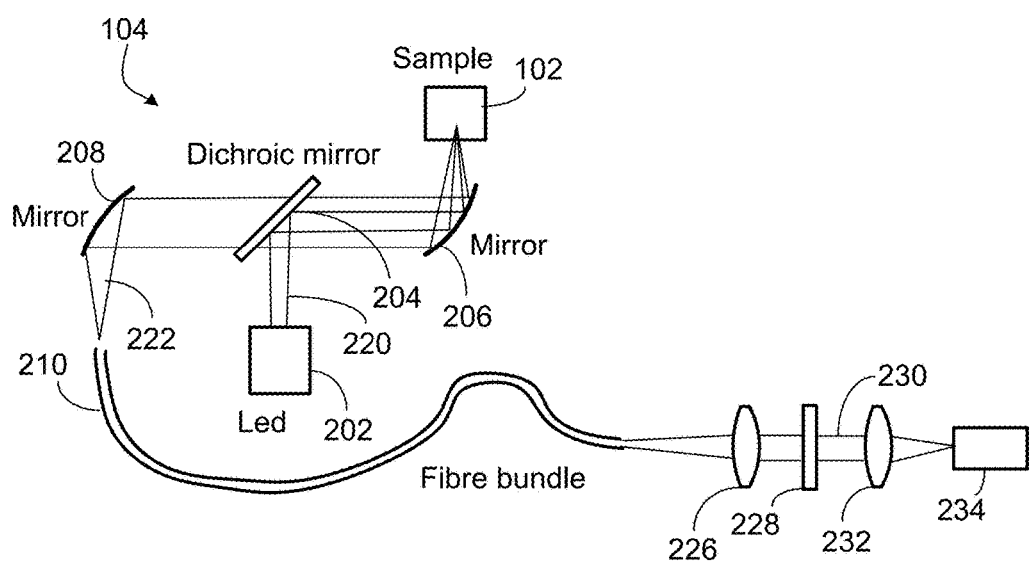

FIGS. 2A and 2B are diagrams illustrating examples of optical instruments 104 as described with reference to FIG. 1. The optical instruments 104 of FIGS. 2A and 2B can be used to perform OCA and to detect the fluorescence signal generated by the analyzed petroleum product sample 102. The example components of the system 100 can include a light source 202, mirrors 204, 206, and 208, lenses 212 and 216, grating 214, and a detector 218. The light source 202 can be a continuous monochromatic light source that is electronically pulsed or a pulsed light source. The pulsed light source can be a light emitting diode (LED), a pulsed laser having a trigger, such as the fourth harmonic or the third harmonic of a Nd:YAG laser, a pumped pulsed dye laser, or a pumped pulsed MOPO laser. The light source 202 generates a light beam 220. For example, the LED source can generate a light beam 220 with a low energy, in the pico-Joule range (for example, smaller than 1 nano-Joule). In some implementations, the light source 202 can be a pulsed wave (CW) collimated laser with a central emission wavelength of 405 nanometers and output power of 20 milliwatts.

The light source 202 can emit a light beam 220 of a single wavelength (for example, laser beam). In some implementations, the light source 202 can be a tunable laser that can emit electromagnetic waves of a plurality of wavelengths within a range of wavelengths. The light beam 220 can be in the visible light spectrum, in the ultraviolet light spectrum, or in the infrared light spectrum. For example, the wavelengths of the electromagnetic waves 105 can be within a range of 200-650 nanometers.

The light source can be guided by the mirrors 204 and 206 towards the petroleum product sample 102. Mirror 204 can be a dichroic mirror that has significantly different reflection and transmission properties at different wavelengths. The dichroic mirror can selectively pass light beams of a small range of wavelengths while reflecting other wavelengths. Mirror 206 can be a parabolic mirror configured to direct the light beam 220 towards the petroleum product sample (for example, through an optical fiber bundle 106, as described with reference to FIG. 1). The light beam 220 crosses the walls of the container (for example, container 108 in FIG. 1) to irradiate the petroleum product sample 102.

The petroleum product sample 102, irradiated by the step laser beam 107, generates a laser-induced fluorescence signal 222. Mirror 206 can be configured to direct the fluorescent signal 222 towards other components of the optical instrument 104. For example, the fluorescent signal 222 can be filtered by the dichroic mirror 204 and/or an optical filter. The filtered fluorescent signal 222 can be directed by mirror 208 towards an optical fiber bundle 210.

In some implementations, as illustrated in FIG. 2A, the optical fiber bundle 210 can direct the fluorescent signal 222 towards a lens 212, for example, a grating. The fluorescent signal 222 can be diverged by the lens 212 on the grating 214. The lens 212 can be configured to spatially separate the fluorescent signal 222 in diffracted light 224 with one or more individual wavelengths or a range of wavelengths. For example, the grating 214 can be configured to produce diffracted light 224 with different wavelengths dependent upon different grating positions. The grating 214 can be a fixed diffraction grating or a rotating diffraction grating.

The diffraction grating in a spectrometer is, in general, rotated via a series of gears to achieve accurate wavelength separation. Gear-driven rotating diffraction grating provides a high resolution (nanometers), but the time required for a complete scan is not suitable for online applications. Gear-driven rotating diffraction grating is generally reserved for laboratory and offline environments. Gear-less fast rotating diffraction grating (as described with reference to FIGS. 3A-3D) can be used in field based applications, providing near real-time results. The gear-less fast rotating diffraction grating can be configured to obtain spectral resolutions of as low as 5-10 nanometers throughout a wide wavelength range from 350 nanometers to 700 nanometers. The gear-less fast rotating diffraction grating can be configured to perform a complete rotation within seconds (for example, in less than 2 seconds).

The diffracted light 224 can be collimated and focused by a lens 216 into a detector 218. If the lens 212 is a fixed diffraction grating, the diffracted light 224 can be projected onto a detector array, such as a CCD, an ICCD or a PMT. If the lens 212 is a rotating diffraction grating, each wavelength of the diffracted light 224 is projected onto a single detector element. Examples of single detector elements include photodiodes, which require moderate to high levels of light energy and photomultiplier tubes (PMTs) that can detect lower levels of light and require high voltage sources for operation.

For real-time classification and characterization of petroleum product, using fluorescence generated from a low energy light source (pico-joules), the photodiode and PMT are not adequate when based on intensity measurements alone because of the limited sensitivity to collect enough photon energy during the wavelength scan time. The photodiode and the PMT can be adapted to real-time classification and characterization of petroleum product by integrating a photon counting multi-scaler detection scheme.

The photon counting multi-scaler detection scheme optoelectronic detector (including either the photodiode or the PMT) is configured to resolve both temporally and spectrally the fluorescence emission profile of the induced petroleum product fluorescence. Photon counting techniques are characterized by high signal to noise ratio (SNR) and are suitable for low light intensity. Photon counting scheme optoelectronic detectors are characterized by high detection stability, such that fluctuations in detector voltage supply do not affect the resistor-capacitor rise time constant (tau).

The photon counting multi-scaler detection scheme optoelectronic detector is configured to obtain the optical intensity by correlating the frequency of photon incidences that occur within particularly defined subsequent time intervals over several periods. Each sequence or measurement period is triggered by the laser pulse. Using the laser pulse as a trigger allows the intensity waveform to be generated from the accumulation of the photon occurrences in each lime interval over each complete period. Photon counting techniques do not present any non-linearities (for example, a photon is either present or not), which removes any issues associated with amplitude noise. The combination of the gear-less rotating diffraction grating and the photon counting multi-scaler detection scheme provides the extraction of maximum amount of information from the fluorescing petroleum sample. The combination of the gear-less rotating diffraction grating and the photon counting multi-scaler detection scheme is essential for real-time applications that require rapid analysis of petroleum product using a low level energy light source.

In some implementations, as illustrated in FIG. 2B, the optical fiber bundle 210 can direct the fluorescent signal 222 towards a lens 226. The fluorescent signal 222 can be diverged by the lens 226 on a filter 228. The filter 228 can be a narrow band filter configured to concentrate the fluorescence signal 222 to a particular narrow region in the fluorescence spectrum. The filtered signal 230, can be focused by a lens 232 into a detector 234. The detector 234 can be any of the detectors described with reference to FIG. 2A.

Figure 3A:
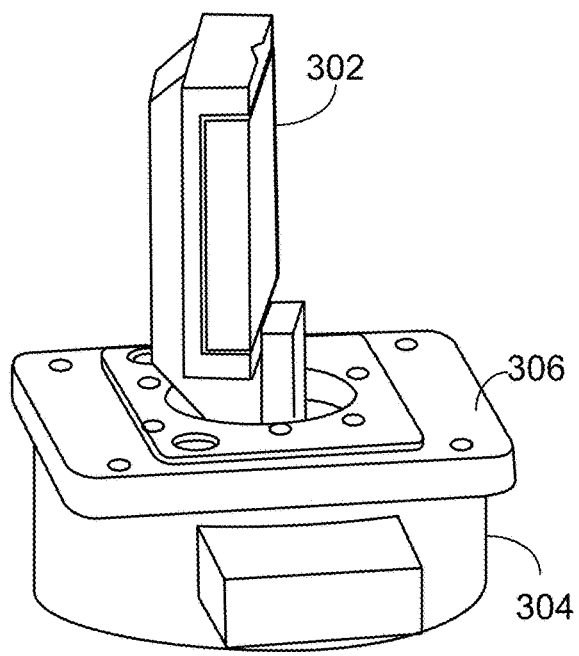
FIGS. 3A-3C show front, top, and side views of an example diffraction grating.
Figure 3B:
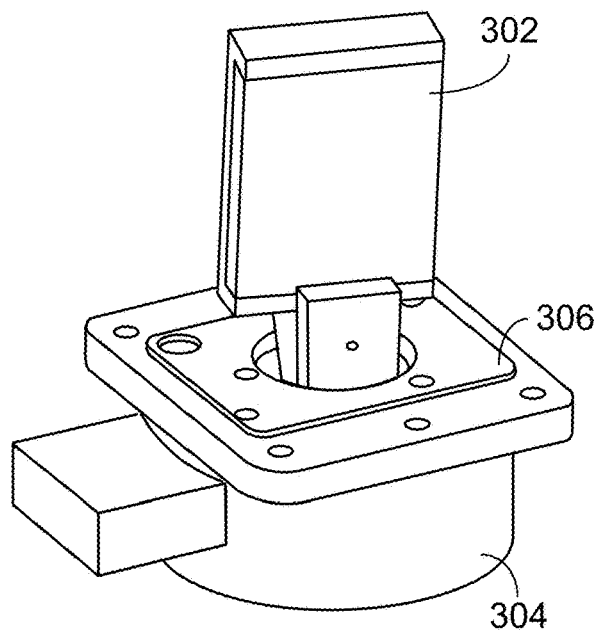
Figure 3C:
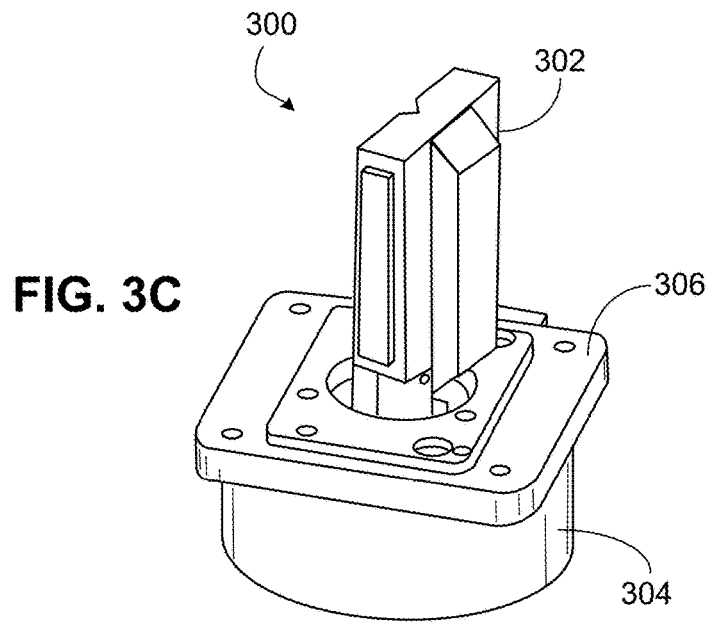

FIGS. 3A-3C show front, top, and side views of an example gear-less fast rotating diffraction grating 300. The example gear-less fast rotating diffraction grating 300 can be used as diffraction grating 214 described with reference to FIGS. 2a and 2B. The example gear-less fast rotating diffraction grating 300 is configured for real-time, online field applications by mounting the diffraction grating 302 directly on the axis of a rotating actuator 304 (for example, a motor). The position of the diffraction grating 302, thus wavelength selection of the grating, can be determined by an integrated decoder. The particular arrangement of the example gear-less fast rotating diffraction grating 300 contributes to the robust nature of the system (reduction in number of parts) and enables a straightforward and rapid scan-time over the complete emission spectra for resolutions down to 5-10 nanometers. From experimental feasibility studies it has been determined that a 10 nanometers resolution is sufficient to classify different petroleum products and to determine the most commonly found cross-product contaminants.

Figure 3D:
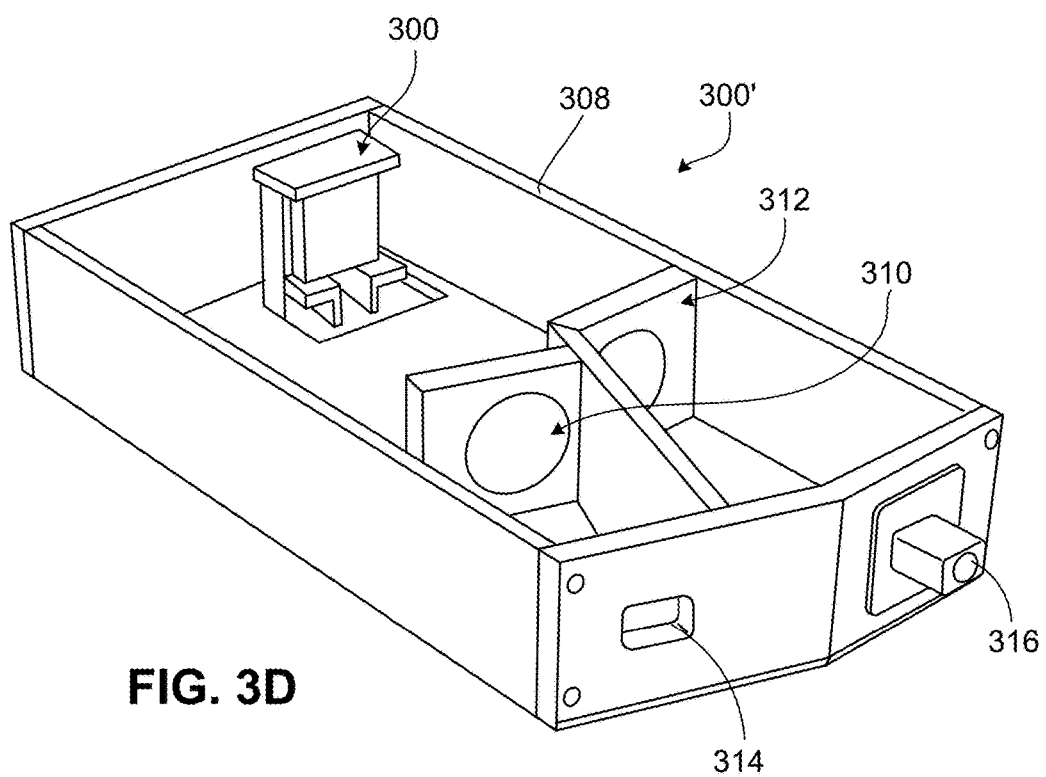
FIG. 3D shows a top view of an example diffraction grating embedded in a housing.

The example gear-less fast rotating diffraction grating 300 can further include a support 306 for attaching the example gear-less fast rotating diffraction grating 300 to a housing 308 of a spectrometer 300', as illustrated in FIG. 3D. The spectrometer 300' can include an entrance slit 310 and an exit slit 312. The entrance slit 310 can be coupled with an optical fiber (for example, optical fiber bundle 210 illustrated in FIG. 2A) directing the fluorescence signal. The exit slit 312 can be coupled with an electronic housing of the detection unit for guiding the diffracted signal to a detector (for example, detector 218 illustrated in FIG. 2A). The spectrometer 300' can include achromatic collimating lens 314 and 316. The collimating lens 314 can increase the resolution of the spectrometer 300' by focusing the fluorescence signal on the gear-less fast rotating diffraction grating 300. The collimating lens 316 can increase the resolution of the spectrometer 300' by focusing the diffracted through the exit slit 312 towards the detector.

Figure 4:
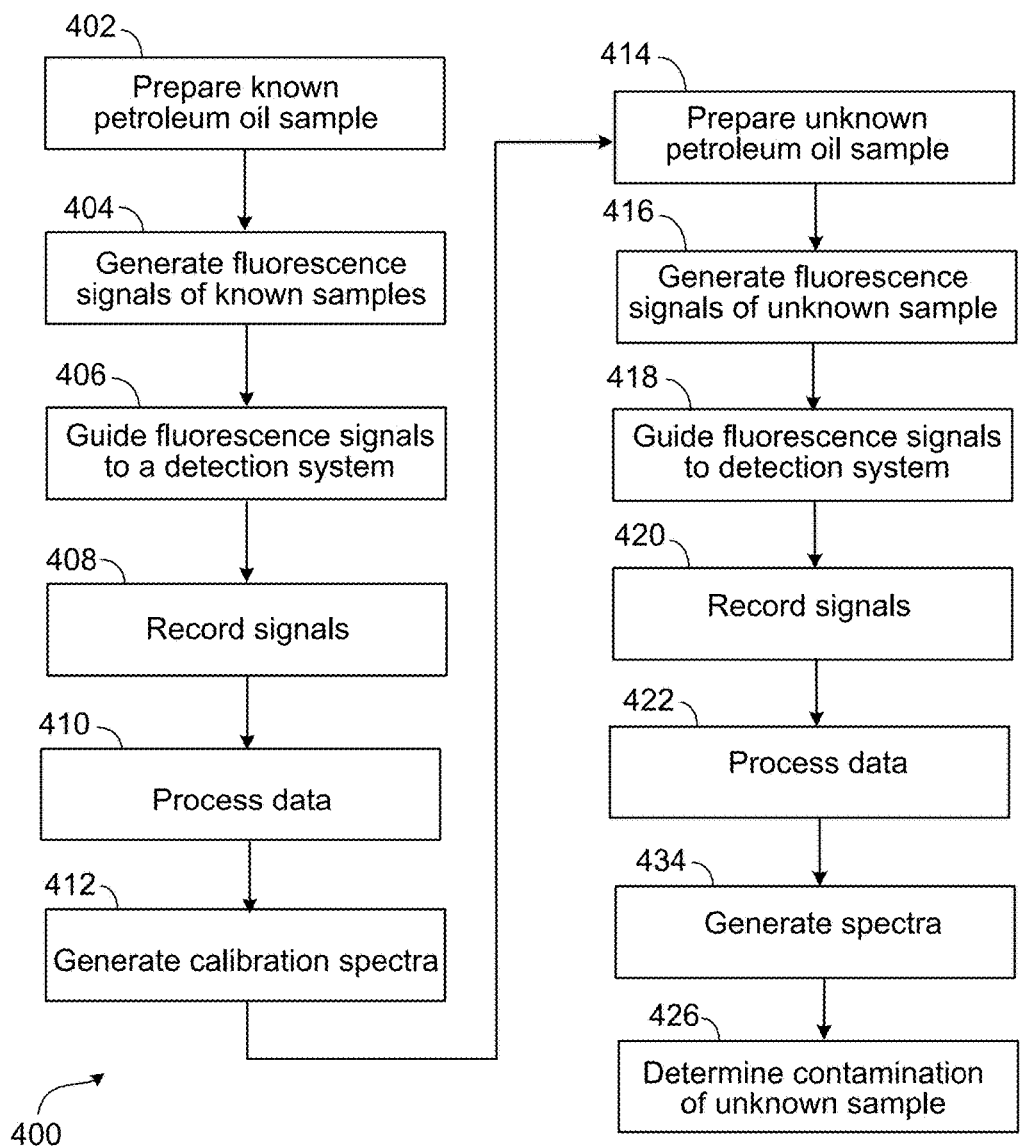
FIG. 4 is a flow chart of an example of a process for characterizing petroleum product contamination using fluorescence signals.

FIG. 4 is a flow chart of a method 400 for diagnosing oil contamination according to an implementation. The method 400 can be executed using the systems described with reference to FIGS. 1 and 3A-3D, in the proximity of a pipeline. However, it will be understood that method 400 can be performed, for example, by any other suitable system, environment, software, and hardware, or a combination of systems, environments, software, and hardware, as appropriate. In some implementations, various steps of method 400 can be run in parallel, in combination, in loops, or in any order.

At 402, a known sample is prepared for analysis. The known sample can be a liquid that comprises fluorescent or phosphorescent molecules. The known petroleum product sample can be a refined petroleum product sample including petroleum gasoline, diesel fuel, kerosene, kerosene B, asphalt base, heating oil, naphtha, and liquefied petroleum gas or crude petroleum products. In some implementations, the known petroleum product sample can be a refined petroleum product sample that is collected immediately after the refinery process. The amount of collected oil sample can be smaller than 1 centiliters (for example, about 1-2 milliliters). The collection of the oil sample can include placing the oil sample in an optically transparent cuvette. The cuvette can be a quartz cuvette with 1 cm optical path length.

At 404, fluorescence signals of the known petroleum product sample are generated. The generation of fluorescence signals includes generating and guiding a light beam to irradiate the known petroleum product sample. The light beam can be an electromagnetic wave of a particular wavelength. For example, the light beam can be a pulsed light beam generated by an LED. The light beam can have low intensity (in pico-Joule range) that is smaller than 1 nano-Joule. The source of the light beam can be setup so that the light beam is incident on the front surface of the cuvette and at a preferred incidence angle (for example, 90 degrees) to the plane of the surface in the horizontal direction. In some implementations, the light source can be setup in a position that is independent from the front surface of the cuvette and the light beam is directed towards the front surface of the cuvette at a preferred incidence angle through an optical system made of one or more lenses, mirrors, and optical fibers.

At 406, the resulting laser-induced fluorescence signal from the petroleum product is guided to a detection system by an optical system including one or more lenses, mirrors, and optical fibers. The detection system can be configured to detect a spectral range from about 350 nanometers to about 700 nanometers. In some implementations, the detection system can include a gear-less fast rotating diffraction grating configured to produce diffracted light with different wavelengths dependent upon different grating positions and a photon counting multi-scaler detection scheme optoelectronic detector (including either the photodiode or the PMT) configured to resolve both temporally and spectrally the fluorescence emission profile of the induced petroleum product fluorescence. In some implementations, the detection system can include a filter, such as a narrow band filter, configured to concentrate the fluorescence signal to a particular narrow region in the fluorescence spectrum and a detector, such as a fast photodiode. Example of narrow wavelength region is 410 nm-430 nm.

At 408, signals are being recorded by the detection system, using particular optical and temporal parameters. The set of optical parameters can include a number of wavelengths (measured fluorescence wavelengths spatially separated by the diffraction grating), measurement resolution (separation distance between each fluorescence wavelength), and first measured wavelength in nanometers. The set of temporal parameters can include a measurement resolution (time separation between each measurements), a time vector (number of time measurements), an acquisition time (time to measure each spatially separated wavelength temporal decay) and a total time (time required to take measurement of full spectral contour diagram). For example, diffracted signals can be captured by a photon counting photodiode as a function of time synchronized with the rotation of the gear-less fast rotating diffraction grating.

At 410, the recorded data is processed. Data processing can include wavelength normalization, smoothing, reduction of redundant information and fitting algorithms. At 412 calibration spectra is generated. Calibration spectra can include contours of equal fluorescence intensities of the time-resolved fluorescence spectra. Calibration spectra can be displayed as contour plots of the fluorescence wavelength emission relative to the time decay. Relative intensities were normalized such that the contour lines reflect the variations in the shapes of the time-resolved fluorescence spectra only and not their relative intensities. Without normalization of the relative intensities of these spectra, the contour diagrams would resemble one another making them useless for oil identification, especially when the UV excitation wavelength is longer than 300 nm. By choosing a different wavelength for normalizing the intensities of the spectra, the contour patterns present different shapes. The normalization with different wavelengths can retain differences between the contour diagrams that can be used as additional pieces of information in the petroleum product identification process. Instead of identifying an oil sampler by a single fingerprint, it is now possible to identify it by a set of fingerprints, each of which is constructed at a different normalization wavelength.

Steps 402 to 412 can be repeated multiple times to generate calibration spectra for each type of petroleum product of interest. The petroleum products of interest can include refined petroleum products that are not contaminated or contaminated with different contaminants of interest. The contaminants of interest can include other types of petroleum products and water. Steps 402 to 412 can be repeated multiple times to generate calibration spectra for each type of petroleum product of interest for different degrees of contamination, expressed in percentage. Steps 402 to 412 can be repeated multiple times to generate calibration spectra for a particular type of petroleum product using different optical and temporal parameters of interest. All generated calibration spectra can be saved in a database for being accessed at a later time without having to repeat steps 402 to 412. To perform an accurate comparative analysis of different fluorescence spectra the same intensity profile is used for each sample.

At 414, an unknown sample is prepared for analysis. The unknown sample can be a liquid that comprises fluorescent or phosphorescent molecules. The unknown sample can be a known type of (refined) petroleum product with an unknown degree of contamination with an unknown contaminant. Preparing the unknown petroleum product sample for analysis can include preparing an optical access to the unknown petroleum product sample. Preparing an optical access to the unknown petroleum product sample can include installing an optical window in a pipeline through which the unknown petroleum product sample is flowing. The optical window can be formed such that it is transparent to the fluorescence signal and the energy light beam in the pipeline.

At step 416, fluorescence signals of the unknown petroleum product sample are generated. The generation of fluorescence signals includes generating and guiding a light beam to irradiate the unknown petroleum product sample. The light beam can be an electromagnetic wave of a particular wavelength. For example, the light beam can be a pulsed light beam generated by an LED. The light beam can have low intensity (in pico-Joule range) that is smaller than 1 nano-Joule. The source of the light beam can be setup so that the light beam is incident on the optical window and at a preferred incidence angle (for example, 90 degrees) to the plane of the optical window. In some implementations, the light source can be setup in a position that is independent from the front surface of the cuvette and the light beam is directed towards the front surface of the cuvette at a preferred incidence angle through an optical system made of one or more lenses, mirrors, and optical fibers.

At step 418, fluorescence signals are guided to the detection system by an optical system including one or more lenses, mirrors, and optical fibers. In some implementations, the detection system used to detect the fluorescence signals generated by the unknown petroleum product sample is similar or identical to the detection system used to detect the fluorescence signals generated by the known petroleum product samples. At step 420, the detected signals are recorded. At step 422, the recoded data is processed. In some implementations, the recording and processing parameters used for the unknown petroleum product sample are similar or identical to the recording and processing parameters used for the known petroleum product samples.

At step 424, the processed data is used to generate spectra for the unknown petroleum product sample. In some implementations, the spectra of the unknown petroleum product sample is generated similarly or identically to the spectra of the known petroleum product samples. At step 426, the spectra is used to determine the contamination of the unknown sample. The contamination determination can include an identification of the contaminant in the known petroleum product base and a quantitative determination of a degree of contamination (expressed in percentages). For example, contamination can be determined by correlating the derived spectra to calibration spectra. In some implementations, the correlation is based on image processing tools to identify a best match within a set of calibration spectra. In some implementations, steps 416 to 426 can be performed in real-time, such that the process starting with the moment when the unknown petroleum product sample is irradiated by the light beam until the contamination is determined is completed within seconds.

The use of any suitable programming language is considered to be within the scope of this specification. OCA oil contamination analysis data can be retrieved (for example, using a suitable database query language) from earlier database to determine a contamination rate. Processing can include a repetition of steps 402-426 at different times (corresponding to different contamination rates). Output of the method 400 can be provided in a standard tabular format, but other formats are possible and considered to be within the scope of this specification.

The method 400 can be used to determine relationships between the OCA parameters (for example, natural frequency or the damping factor) associated with the existing OCA oil contamination analysis data (for example, viscosity) and then graphically display the determined relationship results using a graphical technique, as described with reference to FIGS. 3B and 4.

FIGS. 5A-5D, 6A-6D and 7A-7D illustrate example results obtained using the rotating diffraction grating and photon counting detection scheme corresponding to different not contaminated petroleum product samples. Results 500a of FIGS. 5A-5D, 600a of FIGS. 6A-6D, and 700a of FIGS. 7A-7DA correspond to gasoline A. Results 500b of FIGS. 5A-5D, 600b of FIGS. 6A-6D, and 700b of FIGS. 7A-7D correspond to gasoline B. Results 500c of FIGS. 5A-5D, 600c of FIGS. 6A-6D, and 700c of FIGS. 7A-7D correspond to diesel. Results 500d of FIGS. 5A-5D, 600d of FIGS. 6A-6D, and 700d of FIGS. 7A-7D correspond to kerosene.

Contours of equal fluorescence intensities of the time-resolved fluorescence spectra are displayed as contour plots of the fluorescence wavelength emission (502a of FIGS. 5A-5D, 602a of FIGS. 6A-6D, and 702a of FIGS. 7A-7D) relative to the time decay (502b of FIGS. 5A-5D, 602b of FIGS. 6A-6D, and 702b of FIGS. 7A-7D). Differences between contour diagrams can be associated to the optical and temporal parameters used to determine the results. For example, the results illustrated in FIGS. 5A-5D correspond to a set of optical parameters including 20 wavelengths, 1 nanometer measurement resolution, and first measured wavelength of 353 nanometers. The results illustrated in FIGS. 5A-5D correspond to a set of temporal parameters including 1 nanosecond measurement resolution, a time vector equal to 20, an acquisition time of 200 milliseconds and a total time of 4 seconds. The results illustrated in FIGS. 6A-6D correspond to a set of optical parameters including 10 wavelengths, 2 nanometer measurement resolution, and first measured wavelength of 353 nanometers. The results illustrated in FIGS. 6A-6D correspond to a set of temporal parameters including 2 nanosecond measurement resolution, a time vector equal to 20, an acquisition time of 200 milliseconds and a total time of 2 seconds. The results illustrated in FIGS. 7A-7D correspond to a set of optical parameters including 7 wavelengths, 1 nanometer measurement resolution, and first measured wavelength of 350 nanometers. The results illustrated in FIGS. 7A-7D correspond to a set of temporal parameters including 1 nanosecond measurement resolution, a time vector equal to 20, an acquisition time of 200 milliseconds and a total time of 1.4 seconds.

An initial visual analysis indicates that the fluorescence induced in gasoline A is greater than the fluorescence induced in the other petroleum product types. The lowest fluorescence response is given by the kerosene sample. The temporal decay of the fluorescence emission is greatest for the diesel sample. Using image analysis tools, different petroleum products can be differentiated and characterized. The example display can allow a rapid, visual analysis of the presented data. In some implementations, similar contour plots can be displayed to a user analyzing a particular oil sample, according to method 400.

FIGS. 8A-8F illustrate example results obtained using the rotating diffraction grating and photon counting detection scheme corresponding to different contaminated petroleum product samples. FIGS. 8A, 8C, and 8E illustrate example results obtained using the rotating diffraction grating and photon counting detection scheme corresponding to kerosene A contaminated with 5% diesel derived from data acquired with optical and temporal parameters. FIGS. 8B, 8D, and 8F illustrate example results obtained using the rotating diffraction grating and photon counting detection scheme corresponding to kerosene B contaminated with 5% diesel derived from data acquired with optical and temporal parameters.

The results illustrated in FIGS. 8A and 8B, shown as plots 800*a* and 800*b*, respectively, correspond to a set of optical parameters including 20 wavelengths, 1 nanometer measurement resolution, and first measured wavelength of 353 nanometers. The results illustrated in FIGS. 8A and 8B correspond to a set of temporal parameters including 1 nanosecond measurement resolution, a time vector equal to 20, an acquisition time of 200 milliseconds and a total time of 4 seconds. The results illustrated in FIGS. 8C and 8D, shown as plots 800*c* and 800*d*, respectively, correspond to a set of optical parameters including 10 wavelengths, 2 nanometer measurement resolution, and first measured wavelength of 353 nanometers. The results illustrated in FIGS. 8C and 8D correspond to a set of temporal parameters including 2 nanosecond measurement resolution, a time vector equal to 20, an acquisition time of 200 milliseconds and a total time of 2 seconds. The results illustrated in FIGS. 8E and 8F, shown as plots 800*e* and 800*f*, respectively, correspond to set of optical parameters including 8 wavelengths, 1 nanometer measurement resolution, and first measured wavelength of 350 nanometers. The results illustrated in FIGS. 8E and 8F correspond to a set of temporal parameters including 1 nanosecond measurement resolution, a time vector equal to 20, an acquisition time of 200 milliseconds and a total time of 1.4 seconds. Using image analysis tools, different contaminated petroleum products can be characterized in comparison to non-contaminated corresponding petroleum products or known spectra of contaminated petroleum products. The example display can allow a rapid, visual analysis of the presented data. In some implementations, a similar contour plot can be displayed to a user analyzing a particular oil sample, according to method 400.

Figure 9:
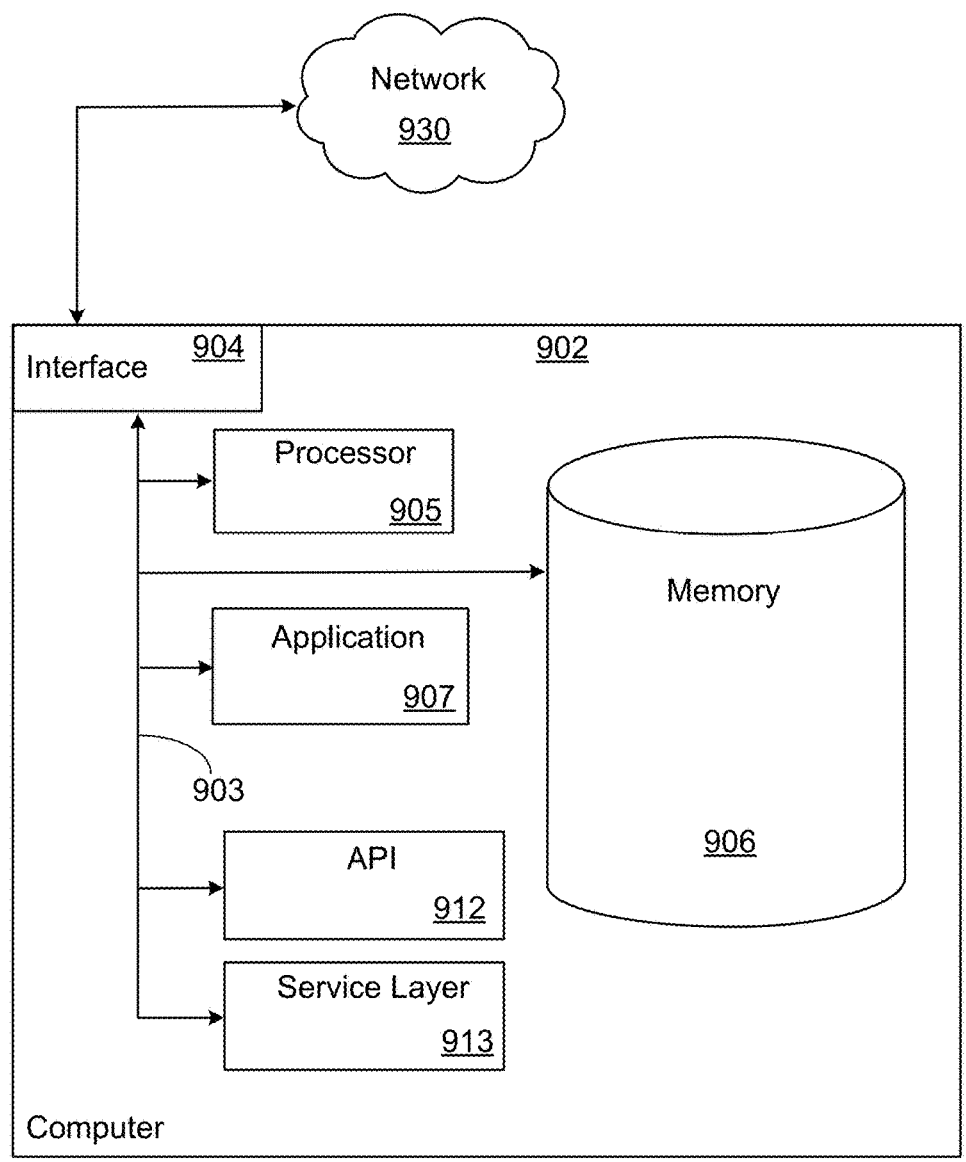
FIG. 9 is a high-level architectural block diagram of an example of a computer system for correlating and predicting OCAs in a petroleum product sample.

FIG. 9 is a block diagram 114 of an example computer 902 used for predicting oil contamination based on OCA in a petroleum product sample according to an implementation. The illustrated computer 902 is intended to encompass any computing device such as a server, desktop computer, laptop or notebook computer, wireless data port, smart phone, personal data assistant (PDA), tablet computing device, one or more processors within these devices, or any other suitable processing device, including both physical and virtual instances of the computing device. Additionally, the computer 902 may comprise a computer that includes an input device, such as a keypad, keyboard, touch screen, or other device that can accept user information, and an output device that conveys information associated with the operation of the computer 902, including digital data, visual and audio information, or a graphical user interface (GUI).

The computer 902 can serve as a client, network component, a server, a database or other persistency, or any other component of a computer system for predicting oil contamination based on OCA in a petroleum product sample. The illustrated computer 902 is communicably coupled with a network 930. In some implementations, one or more components of the computer 902 may be configured to operate within a cloud-computing-based, local, global, or other environment.

At a high level, the computer 902 is an electronic computing device operable to receive, transmit, process, store, or manage data and information associated with predicting oil contamination based on OCA in a petroleum product sample. According to some implementations, the computer 902 may also include or be communicably coupled with an application server, e-mail server, web server, caching server, streaming data server, business intelligence (BI) server, or other server.

The computer 902 can receive requests over network 930 from a client application (for example, executing on another computer 902) and respond to the received requests by processing the said requests in an appropriate software application. In addition, requests may also be sent to the computer 902 from internal users (for example, from a command console or by other appropriate access method), external or third parties, other automated applications, as well as any other appropriate entities, individuals, systems, or computers.

Each of the components of the computer 902 can communicate using a system bus 903. In some implementations, any or all the components of the computer 902, both hardware and software, may interface with each other or the interface 904 over the system bus 903 using an application programming interface (API) 912 or a service layer 913. The API 912 may include specifications for routines, data structures, and object classes. The API 912 may be either computer language-independent or -dependent and refer to a complete interface, a single function, or even a set of APIs. The service layer 913 provides software services to the computer 902 and other components (whether or not illustrated) that are communicably coupled to the computer 902. The functionality of the computer 902 may be accessible for all service consumers using this service layer. Software services, such as those provided by the service layer 913, provide reusable, defined business functionalities through a defined interface. For example, the interface may be software written in any suitable language providing data in extensible markup language (XML) format or other suitable format. While illustrated as an integrated component of the computer 902, alternative implementations may illustrate the API 912 and the service layer 913 as stand-alone components in relation to other components of the computer 902 and other components (whether or not illustrated) that are communicably coupled to the computer 902. Moreover, any or all parts of the API 912 and the service layer 913 may be implemented as child or sub-modules of another software module, enterprise application, or hardware module without departing from the scope of this specification.

The computer 902 includes an interface 904. Although illustrated as a single interface 904 in FIG. 9, two or more interfaces 904 may be used according to particular needs, desires, or particular implementations of the computer 902 and functionality for predicting oil contamination based on OCA. The interface 904 is used by the computer 902 for communicating with other systems in a distributed environment that are connected to the network 930. Generally, the interface 904 comprises logic encoded in software and hardware in a suitable combination and operable to communicate with the network 930. More specifically, the interface 904 may comprise software supporting one or more communication protocols associated with communications such that the network 930 or interface's hardware is operable to communicate signals within and outside of the illustrated computer 902.

The computer 902 includes a processor 905. Although illustrated as a single processor 905 in FIG. 9, two or more processors may be used according to particular needs, desires, or particular implementations of the computer 902. Generally, the processor 905 executes instructions and manipulates data to perform the operations of the computer 902. Specifically, the processor 905 executes the functionality for predicting oil contamination based on OCA in a petroleum product sample.

The computer 902 also includes a memory 906 that holds data for the computer 902 and other components that can be connected to the network 930. For example, memory 906 can be a database storing OCA oil contamination analysis data, and data consistent with this specification. Although illustrated as a single memory 906 in FIG. 9, two or more memories may be used according to particular needs, desires, or particular implementations of the computer 902 and functionality to predict oil contamination based on OCA in a petroleum product sample. While memory 906 is illustrated as an integral component of the computer 902, in alternative implementations, memory 906 can be external to the computer 902.

The application 907 is an algorithmic software engine providing functionality according to particular needs, desires, or particular implementations of the computer 902, particularly with respect to functionality required for predicting oil contamination based on OCA in a petroleum product sample. For example, application 907 can serve as one or more components, modules, and applications described with respect to any of the figures. Further, although illustrated as a single application 907, the application 907 may be implemented as multiple applications 907 on the computer 902. In addition, although illustrated as integral to the computer 902, in alternative implementations, the application 907 can be external to the computer 902.

There may be any number of computers 902 associated with, or external to, a computer system containing computer 902, each computer 902 communicating over network 930. Further, the terms "client," "user," and other appropriate terminology may be used interchangeably, as appropriate, without departing from the scope of this specification. Moreover, this specification contemplates that many users may use one computer 902, or that one user may use multiple computers 902.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Implementations of the subject matter described in this specification can be implemented as one or more computer programs, such as, one or more modules of computer program instructions encoded on a tangible, non-transitory computer-storage medium for execution by, or to control the operation of, data processing apparatus. Alternatively, or in addition, the program instructions can be encoded on an artificially generated propagated signal, such as, a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of one or more of them.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be or further include special purpose logic circuitry, for example, a central processing unit (CPU), an FPGA (field programmable gate array), or an ASIC (application-specific integrated circuit). In some implementations, the data processing apparatus and special purpose logic circuitry may be hardware-based and software-based. The apparatus can optionally include code that creates an execution environment for computer programs, for example, code that constitutes processor firmware, a protocol stack, a database management system, an operating system, or a combination of one or more of them. The present specification contemplates the use of data processing apparatuses with or without conventional operating systems.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components, as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, such as, a CPU, an FPGA, or an ASIC.

Computers suitable for the execution of a computer program can be based on general or special purpose microprocessors, both, or any other kind of CPU. Generally, a CPU will receive instructions and data from a read-only memory (ROM) or a random access memory (RAM) or both. The essential elements of a computer are a CPU for performing or executing instructions and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable storage device, for example, a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, for example, erasable programmable read-only memory (EPROM), electrically erasable programmable read-only memory (EEPROM), and flash memory devices; magnetic disks, for example, internal hard disks or removable disks; magneto-optical disks; and CD-ROM, DVD-R, DVD-RAM, and DVD-ROM disks. The memory may store various objects or data, including caches, classes, frameworks, applications, backup data, jobs, web pages, web page templates, database tables, repositories storing business and dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, for example, a cathode ray tube (CRT), liquid crystal display (LCD), light emitting diode (LED), or plasma monitor, for displaying information to the user and a keyboard and a pointing device, for example, a mouse, trackball, or trackpad by which the user can provide input to the computer. Input may also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a web browser through which a user can interact with an implementation of the subject matter described in this specification, or any combination of one or more such back-end, middleware, or front-end components. The components of the system can be interconnected by any form or medium of wireline or wireless digital data communication, for example, a communication network. Examples of communication networks include a local area network (LAN), a radio access network (RAN), a metropolitan area network (MAN), a wide area network (WAN), worldwide interoperability for microwave access (WIMAX), a wireless local area network (WLAN) using, for example, 902.11 a/b/g/n and 902.20, all or a portion of the Internet, and any other communication system or systems at one or more locations. The network may communicate with, for example, internet protocol (IP) packets, frame relay frames, asynchronous transfer mode (ATM) cells, voice, video, data, or other suitable information between network addresses.

The computing system can include clients and servers. A client and server are generally remote from each other and typically interact through a communication network. The relationship of client and server arises by virtue of computer programs running on the respective computers and having a client-server relationship to each other.

In some implementations, any or all of the components of the computing system, both hardware and software, may interface with each other or the interface using an application programming interface (API) or a service layer. The API may include specifications for routines, data structures, and object classes. The API may be either computer language-independent or -dependent and refer to a complete interface, a single function, or even a set of APIs. The service layer provides software services to the computing system. The functionality of the various components of the computing system may be accessible for all service consumers via this service layer. Software services provide reusable, defined business functionalities through a defined interface. For example, the interface may be software written in any suitable language providing data in any suitable format. The API and service layer may be an integral or a stand-alone component in relation to other components of the computing system. Moreover, any or all parts of the service layer may be implemented as child or sub-modules of another software module, enterprise application, or hardware module without departing from the scope of this specification.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described as acting in certain combinations and even initially claimed as such, one or more features from a claimed combination can in some cases be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing may be advantageous and performed as deemed appropriate.

Moreover, the separation or integration of various system modules and components in the implementations described earlier should not be understood as requiring such separation or integration in all implementations, and it should be understood that the described program components and systems can generally be integrated together in a single software product or packaged into multiple software products.

Accordingly, the earlier provided description of example implementations does not define or constrain this specification. Other changes, substitutions, and alterations are also possible without departing from the spirit and scope of this specification.

What is claimed is:

1. A method to determine contamination in a petroleum-based sample, the method comprising:
   irradiating the petroleum-based sample with a light beam from a light source such that a fluorescence signal is generated;
   guiding, by a mirror, the fluorescence signal to a gear-less rotating diffraction grating, the gear-less rotating diffraction grating spatially separating a fluorescence wavelength from the fluorescence signal;
   detecting, by an optical detector, fluorescence wavelength;
   transforming the fluorescence wavelength into a spectral contour diagram, the spectral contour diagram comprising a fluorescence wavelength variation over time; and
   determining, the contamination in the petroleum-based sample using the spectral contour diagram.

2. The method of claim 1, wherein the sample is a liquid that comprises fluorescent or phosphorescent molecules.

3. The method of claim 1, wherein the sample comprises refined petroleum products or crude petroleum products.

4. The method of claim 1, wherein the sample is irradiated with the light beam as the sample flows through a pipeline.

5. The method of claim 4, further comprising forming an optical window that is transparent to the fluorescence signal and the light beam in the pipeline.

6. The method of claim 1, wherein the optical detector is configured to detect a spectral range from about 350 nanometers to about 700 nanometers in real time.

7. The method of claim 1, wherein detecting the fluorescence wavelengths is performed by a photon counting multi-scaler optoelectronic detector.

8. The method of claim 7, further comprising determining an optical intensity of the fluorescence signal by correlating a frequency of photon incidences detected by the photon counting multi-scaler optoelectronic detector within pre-defined subsequent time intervals over several periods.

9. The method of claim 1, further comprising mounting the gear-less rotating diffraction grating on a rotating axis of an encoded motor.

10. The method of claim 1, further comprising selecting, by an integrated decoder, a wavelength of the gear-less rotating diffraction grating.

11. The method of claim 10, wherein selecting the wavelength comprises rotating the gear-less rotating diffraction grating from a first position to a second position.

12. The method of claim 10, wherein selecting the wavelength comprises generating a spectral range from about 350 nanometers to about 700 nanometers.

13. The method of claim 12, wherein generating the spectral range is completed in about 2 seconds.

14. The method of claim 1, wherein the light source comprises a light-emitting diode.

15. The method of claim 1, wherein the light beam has an intensity in a pico-Joule range and is smaller than 1 nano-Joule.

16. The method of claim 1, wherein the light beam is a pulsed light beam.

17. The method of claim 1, further comprising generating calibration curves based on samples comprising pre-known percentages of contamination.

18. The method of claim 17, wherein determining the contamination based on the spectral contour diagram comprises correlating the spectral contour diagram to the calibration curves.

19. The method of claim 18, wherein correlating the spectral contour diagram to the calibration curves is performed for a particular set of optical parameters and a particular set of temporal parameters.

20. A system to diagnose an oil contamination, the system comprising:
   a gear-less rotating diffraction grating configured to receive a fluorescence signal generated by irradiating a petroleum-based sample with a light beam, the gear-less rotating diffraction grating configured to spatially separate a fluorescence wavelength from the fluorescence signal;
   an optical detector configured to detect a fluorescence wavelength separated from the fluorescence signal by the gear-less rotating diffraction grating; and
   an optical signal processor configured to perform operations comprising:
      transforming the fluorescence wavelength into a spectral contour diagram, the spectral contour diagram comprising a fluorescence wavelength variation over time, and
      determining the oil contamination in the petroleum-based sample using the spectral contour diagram.

21. The system of claim 20, wherein the sample comprises refined petroleum products or crude petroleum products, and wherein the sample is a liquid that comprises fluorescent or phosphorescent molecules.

22. The system of claim 20, wherein the sample is irradiated with the light beam as the sample flows through a pipeline.

* * * * *